(12) United States Patent
Mercey

(10) Patent No.: US 9,739,713 B2
(45) Date of Patent: Aug. 22, 2017

(54) MICROSTRUCTURED CHIP COMPRISING CONVEX SURFACES FOR SURFACE PLASMON RESONANCE ANALYSIS, ANALYSIS DEVICE CONTAINING SAID MICROSTRUCTURED CHIP AND USE OF SAID DEVICE

(71) Applicant: Thibaut Mercey, Paris (FR)

(72) Inventor: Thibaut Mercey, Paris (FR)

(73) Assignee: PRESTODIAG, Villejuif (FR)

( * ) Notice: Subject to any disclaimer, the term of this patent is extended or adjusted under 35 U.S.C. 154(b) by 358 days.

(21) Appl. No.: 14/354,255

(22) PCT Filed: Oct. 25, 2012

(86) PCT No.: PCT/FR2012/052452
§ 371 (c)(1),
(2) Date: Apr. 25, 2014

(87) PCT Pub. No.: WO2013/060989
PCT Pub. Date: May 2, 2013

(65) Prior Publication Data
US 2014/0293284 A1   Oct. 2, 2014

(30) Foreign Application Priority Data
Oct. 26, 2011   (FR) ...................................... 11 59720

(51) Int. Cl.
*G01J 3/44*   (2006.01)
*G01N 21/55*   (2014.01)
(Continued)

(52) U.S. Cl.
CPC ........... *G01N 21/55* (2013.01); *C12Q 1/6816* (2013.01); *G01N 21/553* (2013.01); *G01N 21/253* (2013.01)

(58) Field of Classification Search
CPC .......... G01N 33/54373; G01N 21/553; G01N 2201/02; G01N 2201/08; G01N 2469/00; G01N 21/253
(Continued)

(56) References Cited

U.S. PATENT DOCUMENTS 5,313,264 A   5/1994   Ivarsson et al.
6,862,094 B2   3/2005   Johansen
(Continued)

FOREIGN PATENT DOCUMENTS

EP   2264438 A1   12/2010
FR   2860872 A1   5/2005
(Continued)

OTHER PUBLICATIONS

Coyle et al., "Localised Plasmons in Gold Photonic Nanocavities", Friday Morning, QELS 2002, QFB3 8:45am., p. 257.
(Continued)

*Primary Examiner* — Sunghee Y Gray
(74) *Attorney, Agent, or Firm* — Young & Thompson

(57) ABSTRACT

A microstructured chip (3; 33; 43; 53; 63) for surface plasmon resonance (SPR) analysis, taking the form of a solid formed by: a base (5; 77); an upper surface (4; 44), at least part of which is covered with a metal layer (2; 22; 42; 52; 62); and at least one side surface (55; 66). The chip is characterized in that the aforementioned upper surface is provided with micrometric zones intended to receive species to be analyzed and selected from among n protrusions and m cavities, and in that when n+m≥2 the zones are separated from one another by planar surfaces, with n varying between 1 and j, m varying between 0 and i, and j and i being integers.

3 Claims, 8 Drawing Sheets

(51) Int. Cl.
*C12M 1/00* (2006.01)
*C40B 30/04* (2006.01)
*C40B 60/12* (2006.01)
*G01N 21/552* (2014.01)
*C12Q 1/68* (2006.01)
*G01N 21/25* (2006.01)

(58) Field of Classification Search
USPC ............ 356/301, 445; 435/287.2, 7.1, 7.32; 506/9, 39; 422/69; 436/501
See application file for complete search history.

(56) References Cited

U.S. PATENT DOCUMENTS

| | | | |
|---|---|---|---|
| 7,551,286 | B2 | 6/2009 | Tani et al. |
| 7,576,863 | B2 | 8/2009 | Weibel |
| 7,678,584 | B2 | 3/2010 | Guedon et al. |
| 7,705,989 | B2 | 4/2010 | Chaton et al. |
| 2002/0115224 | A1* | 8/2002 | Rudel ................. B01J 19/0046 436/164 |
| 2005/0213868 | A1 | 9/2005 | Cunningham |
| 2008/0198376 | A1* | 8/2008 | Poponin ............... G01N 21/658 356/301 |
| 2009/0122310 | A1* | 5/2009 | Zhang .................. B82Y 15/00 356/301 |
| 2010/0227769 | A1 | 9/2010 | Schulz et al. |
| 2011/0120554 | A1* | 5/2011 | Chhajed ................. C09D 1/00 136/259 |
| 2011/0267610 | A1* | 11/2011 | Hu ..................... G01N 21/7746 356/301 |
| 2012/0113419 | A1* | 5/2012 | Wang .................... B82Y 15/00 356/301 |
| 2012/0157804 | A1* | 6/2012 | Rogers ................ A61B 5/0422 600/345 |
| 2012/0170033 | A1* | 7/2012 | Zhu ..................... G01N 21/658 356/301 |

FOREIGN PATENT DOCUMENTS

| | | |
|---|---|---|
| JP | 2005337771 A | 12/2005 |
| WO | 2009021964 A2 | 2/2009 |
| WO | 2011014176 * | 2/2011 ............ B82Y 15/00 |

OTHER PUBLICATIONS

Turker et al., "Grating coupler integrated photodiodes for plasmon resonance based sensing", Lab Chip, 2011, vol. 11, pp. 282-287.
Giudicatti et al., "Plasmonic resonances in nanostructured gold/polymer surfaces by colloidal lithography", Physica Status Solidi A, 2010, vol. 207, No. 4, pp. 935-942.
Mannelli et al., "Bioadhesive nanoareas in antifouling matrix for highly efficient affinity sensors", Proc. of SPIE, 2008, vol. 7035, 70350Y, XP002665168.
Rooney et al., "Designing a curved surface SPR device", Sensors and Actuators B, 2006, vol. 114, pp. 804-811.
Valsesia, Andrea, "Fabrication of nanostructured surfaces for the development of advanced biointerfaces", Scientifica Acta 1, 2007, No. 1, pp. 153-157, XP002665167.
International Search Report, dated Jan. 28, 2013, from corresponding PCT application.

* cited by examiner

MICROSTRUCTURED CHIP COMPRISING CONVEX SURFACES FOR SURFACE PLASMON RESONANCE ANALYSIS, ANALYSIS DEVICE CONTAINING SAID MICROSTRUCTURED CHIP AND USE OF SAID DEVICE

FIELD OF THE INVENTION

The present invention relates to a microstructured chip comprising convex surfaces for surface plasmon resonance analysis, to an analysis device containing said microstructured chip, to a method of analysis and to the uses of said device.

Surface plasmon resonance (or SPR) is an optical technique which makes it possible to detect fine variations in physical properties in the immediate vicinity of a surface. This technique is especially known for making it possible to monitor biomolecular interactions in real time, and without labeling (fluorescent or radioactive dye, for example). It makes it possible in particular to describe and quantify interactions between ligands immobilized on a surface and analytes in solution in a sample.

SPR is a physical phenomenon of collective excitation of the electrons of a metal on a metal-dielectric medium interface (said dielectric medium being typically a liquid medium or a gas). For a particular polarization of the incident light (transverse magnetic, or "TM", polarization) on this interface (also referred to as "surface" in the rest of the text) and for an angle known as the "plasmon resonance angle", a resonance phenomenon occurs which is reflected by the coupling of the incident light energy to a surface wave (known as "surface plasmon") propagating parallel to the interface. This physical phenomenon is reflected by a drop in the intensity of the light reflected by the surface. This excitation takes place only for angles of incidence on the surface above the critical angle of total reflection (which can only exist when a radiation goes from a more refringent medium having an optical index n1 to a less refringent medium having an optical index n2, with n1>n2). In this case, the surface plasmon will "probe" the optical thickness at the surface of the metal, on the dielectric medium side, the optical thickness being defined as the product of the refractive index multiplied by the thickness. When these conditions come together, it can then be said that the surface is sensitive to the plasmon effect.

Typically, an incident radiation arrives according to a given angle of incidence on one of the side faces of a chip (generally a prism in the prior art, since it is the simplest method for coupling light on the sensitive surface), one of the faces of which is covered with a metal layer, and said incident radiation is refracted when it enters the prism (owing to the difference in optical index between the medium constituting the prism and the preceding optical medium, generally air) and is reflected on said metal surface. This configuration is well-known to those skilled in the art as the Kretschmann configuration (E. Kretschmann, *The determination of the Optical Constants of Metals by Excitation of Surface Plasmons*, Z Physik 241:313-324 (1971)). Equivalent configurations also exist when the prism is replaced with a diffraction network for coupling the light (Raether configuration: H. Raether in "*Surface Polaritons*", eds. Agranovich and Mills, North Holland Pubi. Comp., Amsterdam, 1982).

The SPR phenomenon can also make it possible to study biomolecular interactions. In this case, ligands are pre-immobilized on the metal surface of the prism in defined zones. Thus, any subsequent attachment of other molecules with these ligands will locally modify the optical thickness at the level of said defined zones, and will therefore cause variations in the resonance conditions and therefore a shift in the resonance angle. This shift is, as a first approximation, proportional to the amount of biomaterial which has come to interact with the ligands. Thus, small molecules will cause a small shift in the angle of incidence, whereas larger molecules will bring about a greater angular shift. Studying the variations in optical reflectivity associated with the resonance phenomenon will make it possible to detect and measure biomolecular interactions and their change over time at the level of the defined zones.

In addition, other optical methods also make it possible to perform such physical phenomena without labeling (resonant mirror, interferometry, surface acoustic waves, quartz microbalance), but these techniques require equipment which is expensive and unsuitable for actual industrial applications.

TECHNICAL PROBLEM

The current SPR systems are bulky, expensive and difficult to implement and do not therefore make it possible to carry out analyses at low costs. Indeed, most of the systems currently sold require complicated measurement strategies and allow measurements only on a very precise (virtually point-like) zone of the surface. The devices which enable analyses of several zones in parallel are very complex and have moving mechanical parts, thus making the system bulky and difficult to use.

For this reason, for several years, a great deal of scientific research has been dedicated to the development of effective, economical SPR optical devices which are easy to use.

Document U.S. Pat. No. 5,313,264 (Ivarsson et al) describes an SPR device using an "angular" interrogation in which the surface to be studied is excited with a convergent beam and the intensity of the reflected beam is observed on a detector. However, this technique does not make it possible to study several zones in parallel, unless several detectors are juxtaposed (reference is made to an essentially "single-point" analysis).

The document "Designing a curved surface SPR device, J. Rooney and E. A. H. Hall, Sensors and Actuators B 114 (2006) 804-811" describes a device which makes it possible to detect a biomolecular interaction on a concave curve spherical substrate. Although said document suggests juxtaposing said device 8 times, the detection elements of the device are also multiplied 8 times, which makes the final device expensive and bulky.

Documents U.S. Pat. No. 6,862,094 (Johansen et al) and U.S. Pat. No. 7,576,863 (Weibel et al) describe an SPR device which uses, not an angular interrogation, but a wavelength interrogation using a monochromator or a source of white light. These devices make it possible to study several biomolecular interactions in parallel, but comprise moving parts, which increases the maintenance operations on the system, and therefore the overall cost for the user.

There are also SPR devices which make it possible to perform imaging and to monitor, at fixed angle of incidence and fixed wavelength, the change in biomolecular interactions in defined zones on a chip. Documents U.S. Pat. No. 7,678,584 (Guédon et al), U.S. Pat. No. 7,576,863 (Weibel et al) and U.S. Pat. No. 7,551,286 (Tani et al) present such SPR devices. Although these devices make it possible to analyze several interactions in parallel, they have moving parts or do not enable a fine analysis of the interaction when no part moves.

Furthermore, all the devices previously described use chips which are expensive by virtue of their fabrication process. Moreover, since the majority of devices are "single-point" devices, the price per analysis point is high.

Moreover, mention may also be made, in the prior art, of document WO 2009/021964 A2 (Maccraith et al) which describes an optical platform intended for detecting analytes by fluorescence. In said document, the upper planar surface of a network of protuberances of paraboloid form is coated with a metallic film and then functionalized with biological species. A fluorescence signal is then excited by virtue of a plasmonic effect generated by the paraboloid geometry of the protuberances, which makes it possible to obtain an incident beam on said metal-film-coated planar surface above the critical angle.

However, in said document, no information can be directly deduced from the characteristics of the plasmon wave itself, since it is used only for the indirect emission of light by luminescence. Furthermore, the working detection surface is a metal-film-coated planar surface, and makes it possible only to carry out an analysis at a precise angle of θ.

Finally, there also exists, in the prior art, numerous documents describing chips which have nanostructures at their surface, and some of which use the localized surface plasmon resonance (LSPR) physical phenomenon. By way of example, the document "*Grating coupler integrated photodiodes for plasmon resonance based sensing*, B. Turker et al., *Conference on lasers and Electro-Optics* 2011" describes biochips which have at their surface nanostructures arranged according to a periodic network. This network of nanostructures is used for coupling incident light to the plasmon wave of the metal/dielectric interface of the network. The document "Localised plasmons in gold photonic nanocavities, S. Coyle et al., Quantum Electronics and Laser Science Conference 2002" presents, for its part, a nanostructured surface with gold nanocavities. These gold nanocavities involve the localized surface plasmon resonance (LSPR) physical phenomenon which differs from the SPR phenomenon and which leads to an amplification of the plasmonic signals.

Thus, in the abovementioned two documents, not only is the production of networks and cavities on a nanometric scale difficult, but it is also necessary to make use of mobile parts for evaluating the variation in reflectivity of the metallic layer according to the angle of incidence of the light beam.

Lastly, the most compact devices use chips the surface of which is concave. However, it is difficult and expensive to produce a concave part.

There is therefore a real need for a compact SPR device which does not have any moving parts, which is economical, and which comprises a chip that is simple to produce, thus allowing low-cost SPR analyses to be carried out.

DESCRIPTION OF THE INVENTION

The present inventor has found that a device for SPR analysis comprising a microstructured chip which has a particular architecture makes it possible to satisfy these requirements.

The term "chip" or "microstructured chip" will be used without distinction in the rest of the text.

The term "radiation" or "beam" will be used without distinction in the rest of the text.

MICROSTRUCTURED CHIP

Figure 1:
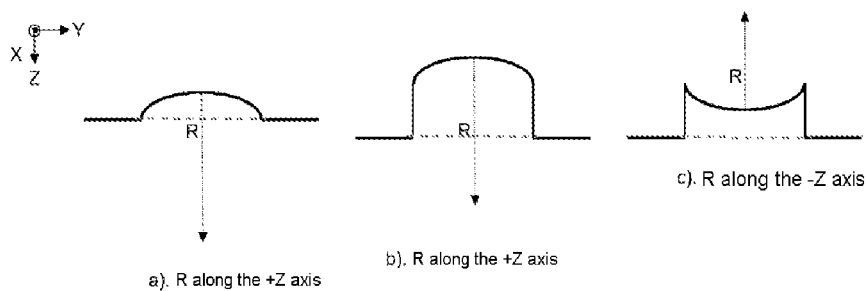
FIG. 1 represents a sectional view of the protuberances according to various embodiments of the invention.

A first subject of the invention is a microstructured chip for surface plasmon resonance (SPR) analysis which is in the form of a solid consisting of a base, of an upper face, at least one part of which is covered with a metal layer, and of at least one side face, characterized in that said upper face is provided with zones of micrometric size intended to receive species to be analyzed chosen from n protuberances and m cavities; and in that when n+m≥2, said zones are separated from one another by planar surfaces, with n ranging from 1 to j and m ranging from 0 to i, j and i being integers.

According to one particular embodiment, the chip contains no cavities (m=0). In other words, the upper face of the chip is provided with zones of micrometric size intended to receive species to be analyzed, which zones are chosen uniquely from at least one protuberance.

According to another embodiment, m is not 0 (m>0). In other words, the upper face of the chip is provided with zones of micrometric size intended to receive species to be analyzed, which zones are chosen from at least one protuberance and at least one cavity.

The term "microstructured chip" is intended to mean a chip which has zones of micrometric size intended to receive species to be analyzed. Thus, the chip is not necessarily of micrometric size, but comprises zones which are of micrometric size.

The term "zones of micrometric size" is intended to mean zones which have at least two dimensions out of three that are of micrometric size, said micrometric dimensions ranging from 1 µm to 1000 µm, and preferentially from 10 µm to 500 µm.

The third dimension of the zone is not therefore necessarily micrometric and can exhibit distances of between 1 mm and 20 mm, preferably between 1 mm and 10 mm.

The zones according to the invention exhibit particular geometries in the form of protuberances an optionally of cavities which will be subsequently described. It is at the level of these zones covered with a metal layer that the plasmon effect will be observed.

According to the invention, the chip comprises a number of zones (i.e. n protuberances and m cavities) of between 1 (when m=0 and n=1) and 500 000, preferably between 10 and 10 000 and more preferentially between 25 and 400.

According to the invention, at least one part of the upper face is coated with the metal layer. It represents the working detection surface (also subsequently referred to as sensitive surface). According to the invention, at least one zone of micrometric size, chosen from n protuberances and m cavities, is coated with the metal layer.

According to one particular embodiment, the upper face is entirely covered with the metal layer.

Thus, according to one particular embodiment combined with the preceding one, not only the zones but also the planar surfaces separating said zones are intended to receive species to be analyzed.

In order to facilitate the description which follows, the direct orthonormal reference frame (XYZ) is used in which the planar surfaces separating the zones are parallel to the plane (XY) and in which the Z axis is oriented downward.

The term "planar surfaces" is intended to mean planar or substantially planar surfaces which may exhibit some defects.

The planar surface separating two zones intended to receive species to be analyzed is referred to as inter-zone surface. Thus, the following terms will be used without distinction: planar surfaces or inter-zone surfaces or else inter-zone planar surfaces. More specifically:
  when the planar surface separates two zones which are cavities, the term inter-cavity surface is used;
  when the planar surface separates two zones which are protuberances, the term inter-protuberance surface is used; and
  when the planar surface separates a zone which is a cavity and another zone which is a protuberance, the term inter-cavity-protuberance surface is used.

According to one embodiment, the zones are arranged in the form of a matrix on the upper face of the chip. Thus, the planar surfaces separate the zones both along the X axis and along the Y axis.

According to another embodiment, the zones are arranged in the form of continuous gutters along the upper face of the chip. Thus, according to this embodiment, the planar surfaces separate the zones on the X axis or along the Y axis.

According to one embodiment, when n+m≥2, the zones are separated by a distance D along the Y axis and by a distance D' along the X axis by the planar surfaces (or inter-zone surfaces); D and D' being between 0 µm (in the case of a continuous gutter along one of the X or Y axes) and 5 mm, preferably between 50 µm and 5 mm, preferably between 200 and 1000 µm and particularly preferably between 300 and 700 µm.

According to one embodiment, when n+m≥2, the zones are separated by a center-to-center CTC distance of between 10 µm and 25 000 µm, preferably between 50 µm and 5000 µm and more preferentially between 100 µm and 1000 µm.

According to one embodiment, the planar surfaces are in planes parallel to the plane (XY); the upper face is then in the form of staircase steps.

According to another embodiment, the planar surfaces are in the same plane (XY) (i.e. Z is constant).

The term "protuberance" is intended to mean an outgrowth on the upper face of the chip, said outgrowth being between two planar surfaces (also referred to as inter-zone surfaces).

The protuberance can be defined either in 3 dimensions (XYZ reference frame) or in two dimensions (section in one plane).

Thus, the term "protuberance" is given to a volume of which all the coordinates are above an imaginary plane connecting the two inter-zone planar surfaces adjacent to said protuberance.

The protuberance will subsequently be described in the plane (YZ).

Thus, a protuberance according to the invention, described in the plane (YZ), is defined by at least one curve which has a mean radius of curvature R and/or at least one straight line.

When the protuberance is defined only by a curve, then the curve is necessarily convex (i.e. radius of curvature along the +Z axis).

When the protuberance is defined by at least one curve and at least one straight line, then the curve may be either concave (i.e. radius of curvature along the −Z axis), or convex.

According to one particular embodiment, the protuberance is defined by two straight lines separated by a curve.

According to one particular embodiment combined with the preceding one, the two straight lines are parallel.

According to another embodiment which can be combined with the preceding one, the two straight lines have different dimensions.

The term "cavity" is intended to mean a hollow in the upper face of the chip, said hollow being between two planar surfaces (also referred to as inter-zone surfaces).

The cavity can be defined either in three dimensions (XYZ reference frame) or in two dimensions (section in one plane).

Thus, the term "cavity" is given to a volume of which all the coordinates are in an imaginary plane connecting the two inter-zone planar surfaces adjacent to said cavity.

The cavity will subsequently be described in the plane (YZ).

Thus, a cavity according to the invention is described in the plane (YZ) and is defined by at least one curve having a mean radius of curvature R and/or at least one straight line.

When the cavity is defined only by a curve, then the curve is necessarily concave (i.e. radius of curvature along the −Z axis).

When the cavity is defined by at least one curve and at least one straight line, then the curve may be either concave or convex (i.e. radius of curvature along the +Z axis).

According to one particular embodiment, the cavity is defined by two straight lines separated by a curve.

According to one particular embodiment combined with the preceding one, the two straight lines are parallel.

According to another embodiment which can be combined with the preceding one, the two straight lines have different dimensions.

Thus, according to one particularly preferred embodiment, the zones of the chip (n protuberances and m cavities), described in the plane (YZ), are defined only by a curve having a mean radius of curvature R (concave for a cavity and convex for a protuberance); the radius of curvature R being between 0.1 mm and 600 mm, preferably between 0.3 mm and 300 mm.

By way of example, mention may be made of n protuberances and m cavities of hemispherical, semi-elliptical or semi-cylindrical shape (reference frame (XYZ)).

According to one preferred embodiment of the invention, the n protuberances and m cavities have a semi-cylindrical shape in the reference frame (XYZ).

According to one particular embodiment, the radius of curvature of the zones (i.e. of the n protuberances and the m cavities) is perpendicular to the plane (XY), i.e. along the Z axis.

According to another embodiment, the radius of curvature of the zones is not perpendicular to the plane (XY) (i.e. the n protuberances and the m cavities have a tilt).

According to one particular embodiment, the zones intended to receive species to be analyzed (the n protuberances and m cavities) have an identical radius of curvature R.

According to the invention, the base of the chip may be a planar or curved surface, or a ridge, or an apex.

According to one preferred embodiment, the base of the chip is a planar surface which is preferably parallel to the planar surfaces (also referred to as inter-zone surfaces).

According to another embodiment which can be combined with the preceding one, the planar surfaces are in the same plane (XY). In other words, if the base is parallel to said planar surfaces, the distances between the planar surfaces and the base of the chip are identical. In this case, it is said that the upper face is parallel to the base.

According to another embodiment, the planar surfaces are in multiple planes parallel to the plane (XY). In other words, if the base is parallel to said planar surfaces, the distances between the planar surfaces and the base of the chip are different (upper face in the form of a staircase step).

The expression "distances between the planar surfaces (or inter-zone surfaces) and the base" refers to heights of the chip, i.e. to the length of the perpendicular connecting the surfaces to the base or to an extension of the base.

According to the invention, the side face(s) of the chip may be planar (perpendicular or not perpendicular to the base and/or to the upper face of the chip) or curved.

According to one preferred embodiment, the side face(s) of the chip is (are) planar.

According to another preferred embodiment, at least one side face of the chip is perpendicular to the base and/or to the upper face.

According to another embodiment, the upper face is parallel to the base of the chip.

According to one particular embodiment of the invention, the chip is joined to a prism well-known from the prior art.

Thus, according to one particular embodiment, the chip is in the form of a parallelepiped (i.e. a chip which has planar surfaces in the same plane (XY) and a base parallel to said planar surfaces). According to this embodiment, the heights of the side surfaces have small dimensions of about from 0.1 mm to 20 mm, preferably from 1 mm to 10 mm.

The term "species to be analyzed" is intended to mean, for example, materials, gases or biological species such as single-stranded or double-stranded DNA, proteins, bacteria, toxins, viruses, mycoplasmas, chemical agents or any other biological or chemical species capable of interacting with other biological or chemical species.

According to one preferred embodiment, the species to be analyzed are biological species, such as pathogenic bacteria, for instance *Salmonella* spp., *Listeria monocytogenes*, *Clostridium difficile*, or else *Campylobacter* spp.

The present inventor has demonstrated that it is possible, by using the chip according to the invention, to advantageously study shiga toxin-producing *Escherichia coli* (STEC) strains, since it enables the simultaneous analysis of large molecules (bacteria themselves), but also of small toxins that they produce.

According to another embodiment of the invention, the n protuberances and m cavities will be functionalized with various biomarker-specific monoclonal antibodies.

FIG. 1 represents a section along the plane (ZY) of a protuberance according to various embodiments. In each of these figures, the protuberance is represented by a surface in the plane (XY) (or by a volume in the XYZ reference frame), all the points of which are located above (negative Z) an imaginary straight line represented by dashes (or imaginary plane in the XYZ reference frame for a volume) connecting the two planar surfaces adjacent to the protuberance:
- in case a): the protuberance is defined solely by a convex-shaped curve with a radius of curvature R (i.e. having a radius of curvature along the +Z axis);
- in case b): the protuberance is defined by two parallel straight lines separated by a curve with a radius of curvature R of convex shape;
- in case c): the protuberance is defined by two parallel straight lines separated by a curve with a radius of curvature R of concave shape (i.e. having a radius of curvature along the −Z axis).

Figure 2:
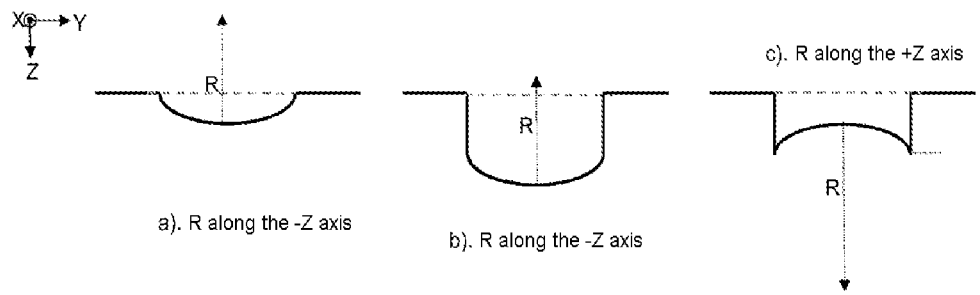
FIG. 2 represents a sectional view of the cavities according to various embodiments of the invention.

FIG. 2 represents a section along the plane (ZY) of a cavity according to various embodiments. In each of these figures, the cavities represented by a surface in the plane (XY) (or by a volume in the XYZ reference frame), all the points of which lie below (positive Z) an imaginary straight line represented by dashes (or imaginary plane in the XYZ reference frame for a volume) connecting the two planar surfaces adjacent to the cavity:
- in case a): the cavity is defined solely by a concave-shaped curve with a radius of curvature R (i.e. having a radius of curvature along the −Z axis);
- in case b): the cavity is defined by two parallel straight lines separated by a concave-shaped curve with a radius of curvature R;
- in case c): the cavity is defined by two parallel straight lines separated by a curve with a radius of curvature R of convex shape (i.e. having a radius of curvature along the +Z axis).

Figure 3:
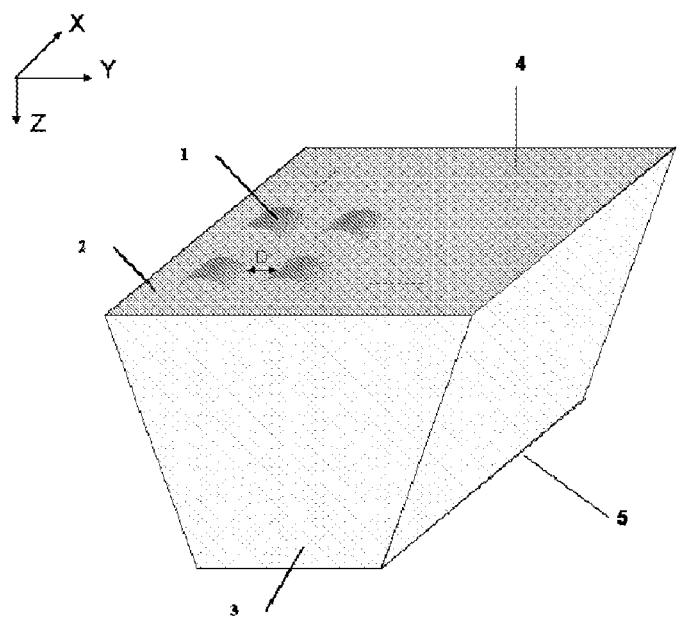
FIG. 3 represents a microstructured chip according to the invention which has protuberances arranged in the form of a matrix.

FIG. 3 represents a microstructured chip 3, in which the upper face 4, comprising inter-protuberance planar surfaces, is parallel to the base 5 of the chip 3. The upper face 4 is covered with a metal layer 2 and is provided with protuberances 1 sensitive to the plasmon effect, intended to receive species to be analyzed.

In FIG. 3, the protuberances 1 are separated from one another by a distance D along the Y axis and by a distance D' along the X axis, by planar surfaces (also referred to as inter-protuberance surfaces).

The microstructured chip 3 can be made of any type of material which allows the propagation of light. Mention may be made, for example, of glass, a crystal or plastics.

According to one preferred embodiment, for cost reasons, the chip 3 is made of plastic(s), for instance PMMA (poly (methyl methacrylate)), PC (polycarbonate), PS (polystyrene), SU-8 (epoxy-based negative photosensitive resin) or PDMS (polydimethylsiloxane).

According to one particular embodiment, when the chip is joined to a prism, it may be made of a material different from that of the prism.

The metal layer 2 which covers the upper layer 4 of the chip 3 (and particularly the protuberances 1) can be made of various metals such as gold, silver, platinum or aluminum.

According to one preferred embodiment, the metal layer is made of gold because of the very good anticorrosive properties of the latter.

The thickness of the metal layer 2 is between 10 and 200 nm, preferably between 30 and 100 nm and even more preferentially between 40 nm and 50 nm.

According to another embodiment combined with the preceding ones, a thin layer of chromium is used as a layer for preattachment of the gold to the upper face 4 of the chip 3.

Figure 4:
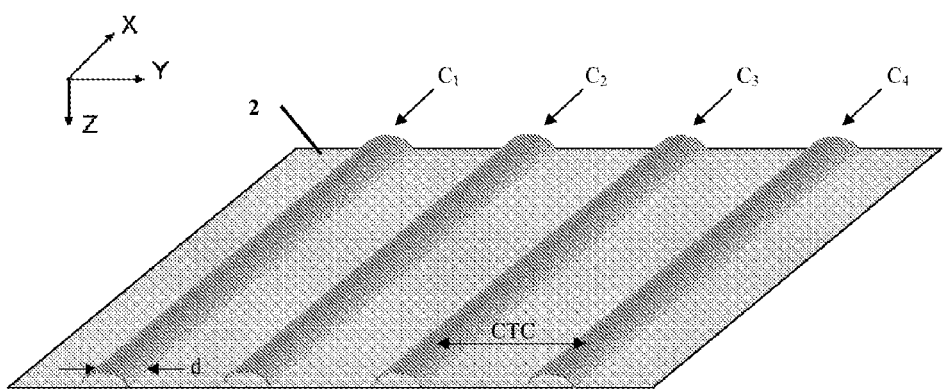
FIG. 4 represents the upper face of a microstructured chip according to the invention which has protuberances arranged in the form of gutters along the X axis.

FIG. 4 represents the upper face of a microstructured chip according to the invention which is entirely covered with a metal layer 2; said microstructured chip is provided with protuberances which are arranged in the form of gutters along the X axis, thus forming four columns $C_1$-$C_4$. In FIG. 4, d represents the diameter of the gutter and CTC represents the center-to-center distance between two successive gutters.

The chip according to the invention makes it possible to adjust the sensitivity of each zone (i.e. of the n protuberances and m cavities) in order to study very different biological species.

According to one embodiment, at least one of the n protuberances and m cavities has a radius of curvature different from the others.

Figure 5:
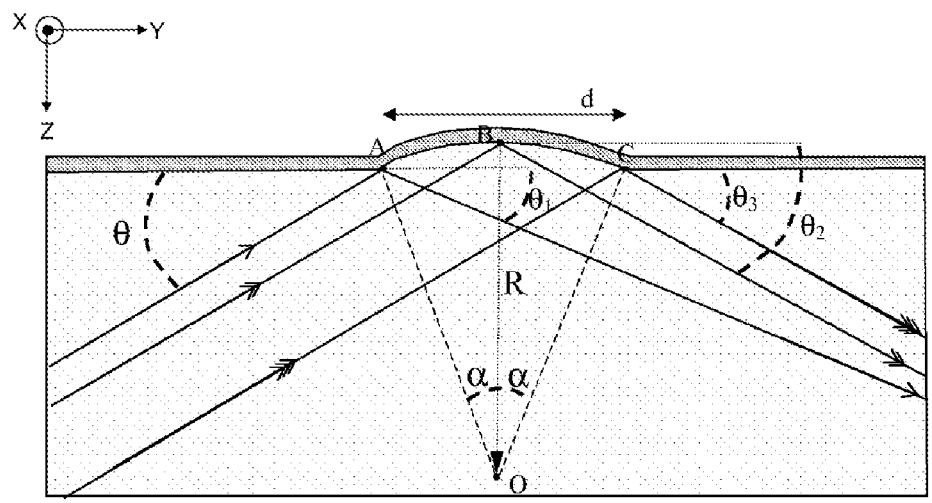
FIG. 5 represents a sectional view of a protuberance without tilt, irradiated by a collimated and polarized monochromatic incident radiation.

FIG. 5 represents an enlargement of a sectional view of FIG. 3 of the convex-surface protuberance 1 of the chip 3 (covered with the metal layer 2) which is irradiated by a monochromatic collimated beam which has an angular incidence θ and is linearly polarized following TM polarization.

The protuberance, which is semi-cylindrical in shape (in the XYZ reference frame), and which has a surface defined by a single curve (in the plane ZY) in FIGS. 3 and 5, is characterized by its radius of curvature R and by the two half-angles α (thus defining a total angle of 2α).

The radius of curvature R and the half-angle α will thus define the length of the chord d, or else the diameter of said cavity.

Owing to the reflection on the sensitive surface (or protuberance 1), the angle of incidence on the two ends A and C will be respectively, for a mean angle of incidence of the collimated beam of θ, $θ_1=θ-2α$ and $θ_3=θ+2α$. Thus, the beam reflected ($θ_1$ for the point A, $θ_2$ for the point B, $θ_3$ for the point C) by said protuberance 1 has an angular width Δθ (Δθ=$θ_3$-$θ_1$) equal to 4α, centered about the angle $θ_{mean}$ (corresponding to the angle $θ_2$ in FIG. 5). In this case, $θ_{mean}=θ_2=θ$.

It is important to note that the choice of the radius of curvature R of the n protuberances and m cavities of the chip according to the invention is very important since it will determine, according to the essential physical parameters (optical index of the chip $n_p$, optical index of the external dielectric medium $n_e$, mean angle of incidence of the collimated beam θ and the size of the biological species that it is desired to analyze), the sensitivity and the angular dynamics of the measurement for each of the n protuberances and m cavities.

The expression "angular dynamics of the measurement" is intended to mean the angular range that it will be possible to visualize during the analyses.

The term "sensitivity" is intended to mean the smallest variation in optical thickness that it will be possible to measure on the sensitive surface.

Indeed, if the radius of curvature is very large, this will draw closer to a plane, therefore the angles $θ_1$ and $θ_3$ will be very close (the angular range of analysis Δθ will therefore be very small), making this configuration particularly suitable for the analysis of small molecules (i.e. good sensitivity). Conversely, a very small radius of curvature will make it possible to observe the plasmon curve in its entirety, with admittedly a measurement sensitivity which is lower, but more suitable for the analysis of large molecules.

It is thus possible, according to the invention, to adapt the measurement sensitivity for various studied species.

According to another embodiment which can be combined with the preceding one, at least one of the n protuberances and m cavities exhibits a tilt of an angle β.

According to this embodiment, the radius of curvature R is deflected relative to the Z axis.

Figure 6:
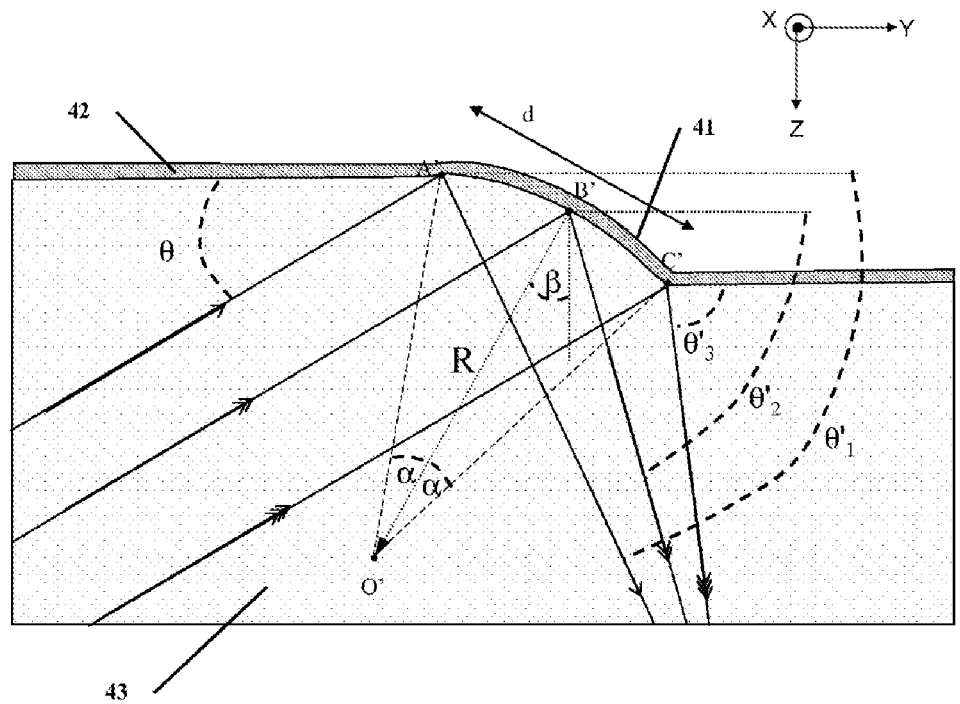
FIG. 6 represents a sectional view of a protuberance which has a tilt of an angle β, irradiated by a collimated and polarized monochromatic incident radiation.

FIG. 6 represents an enlargement of a sectional view of a convex-surface protuberance 41 of a chip 43 (the upper face of which is covered with a metal layer 42) which exhibits a tilt of an angle β and which is irradiated by a collimated monochromatic beam with a mean angle of incidence θ, which is linearly polarized according to the transverse magnetic TM direction.

In the case of a tilt β of the sensitive surface (in this case of the protuberance) relative to the perpendicular to the mean plane of the sensitive surface, the mean plane being defined as the plane parallel to the inter-protuberance planar surfaces, the reflected beam will still have an angular width Δθ which is equal to 4α, but which is this time centered about the mean angle $γ'_{mean}$ (represented by $θ_2$ in FIG. 3) such that $γ'_{mean}=θ+2β$ for a convex surface.

According to one embodiment, the angle β is defined in the following way: 0°<β≤80°, preferably 15°≤β≤45°.

It is thus possible, according to the invention, to adjust, for each of the n protuberances and m cavities, both the angular width studied and also the mean angle (i.e. $θ_2$ or $θ'_2$ represented in FIGS. 5 and 6 depending on whether or not the protuberance is tilted) of this angular range, thus making it possible to adjust the measurement sensitivity for various species within the same chip, during the same experiment.

Thus, according to one particular embodiment, at least one of the zones (i.e. at least one of the n protuberances and m cavities) has both a different radius of curvature and a different orientation compared with the other zones of the chip.

According to another embodiment, which can be combined with the preceding ones, at least one distance between the base and the planar surfaces (also referred to as inter-zone surfaces) is different from the others.

Figure 7:
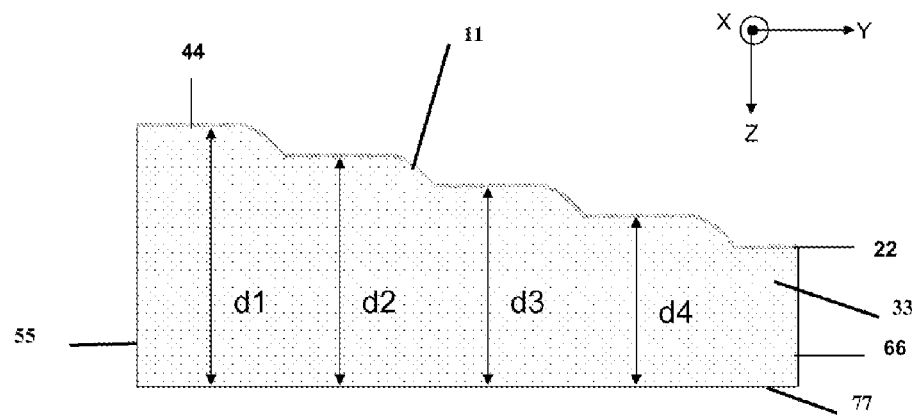
FIG. 7 represents a chip according to one embodiment of the invention which has different distances between the planar surfaces separating the protuberances and the base.

FIG. 7 represents a chip 33 of which the upper face 44, which is covered with a metal layer 22, is provided with curve-shaped protuberances 11. The side faces (55, 66) of the chip 33 are perpendicular to the base 77 and to the planar surfaces.

The distances separating the planar surfaces between the protuberances 11 (or inter-protuberance surfaces) and the base 77 are all different from one another, with d4<d3<d2<d1. In FIG. 7, the inter-zone surfaces are in multiple planes parallel to the plane (XY) (5 planes represented).

The chip according to the invention can be produced by various methods, which necessarily comprise a step of fabricating the chip followed by a step of depositing at least one thin metal layer.

Among the fabrication methods, mention may be made of high-pressure injection, direct mechanical machining, hot stamping, plasma etching, photolithography or laser ablation.

According to one preferred embodiment, the chip is manufactured by high-pressure injection molding.

Production of the chip according to the invention necessarily makes use of a mold having a concave shape to produce a convex-shaped protuberance, thus allowing its production cost to be decreased. Specifically, those skilled in the art will know that the most expensive step when setting up a high-pressure injection molding process to produce components is the production of the mold (or master). The fact that the final surface of the part to be produced contains convex protuberances makes it possible to use a mold with concave shapes, which can be obtained by removing material from the master, which is very simple to do using conventional mechanical machining methods.

Among the methods for depositing thin metal layers, mention may be made of sputtering, vacuum evaporation techniques, or cold deposition techniques.

The cold deposition techniques are of use in particular in the case of a plastic support since the plastic cannot withstand large increases in temperature.

Analysis Device

Figure 8:
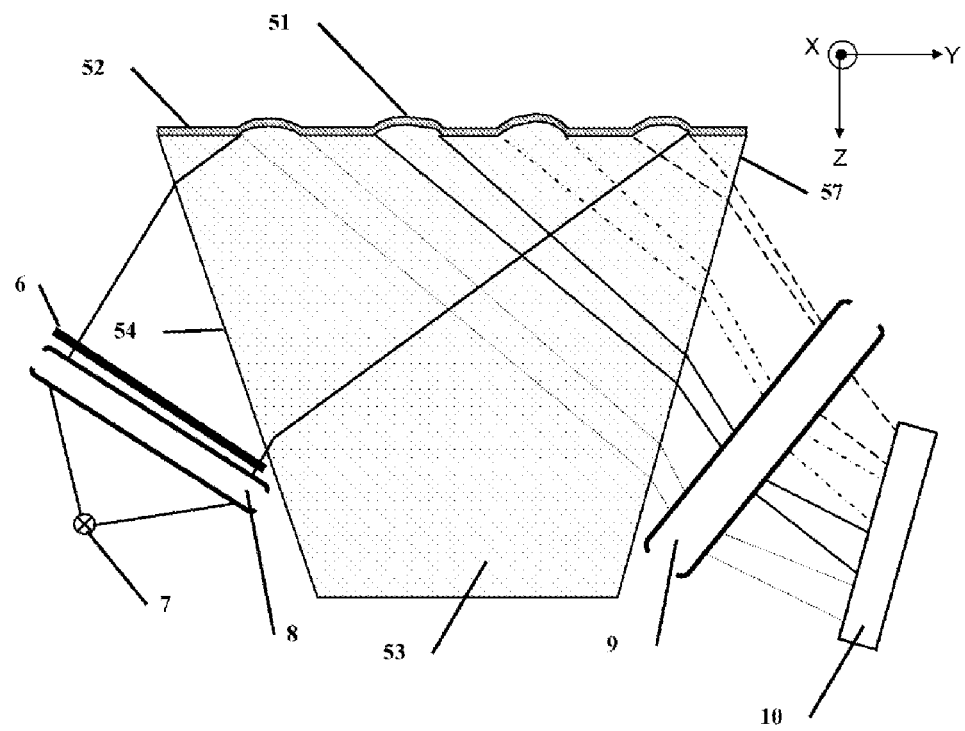
FIG. 8 represents a device comprising a microstructured chip which has identical distances between the planar surfaces separating the protuberances and the base.
Figure 9:
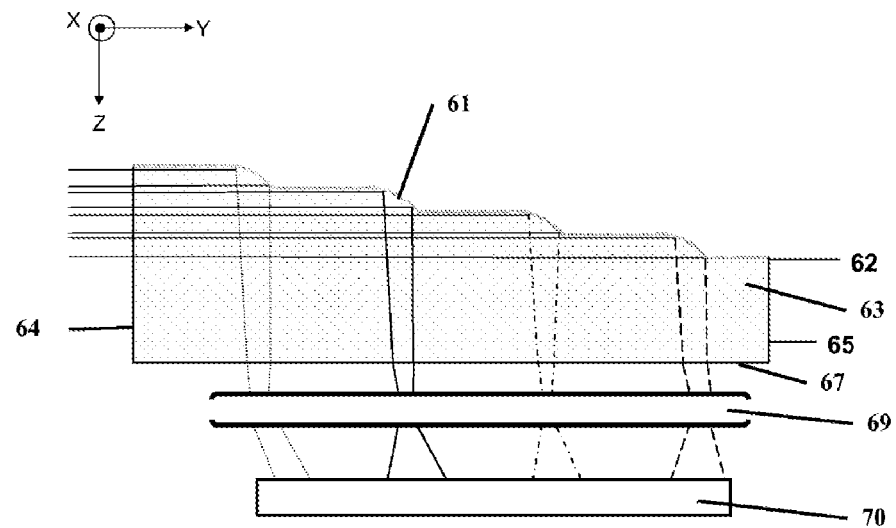
FIG. 9 represents a device comprising a microstructured chip which has different distances between the planar surfaces separating the protuberances and the base.

FIGS. 8 and 9 represent different embodiments of measuring devices comprising the microstructured chip previously described.

Thus, another subject of the present invention is a device for SPR analysis comprising:
 a light source 7 intended to generate an incident beam;
 optionally an optical collimation system 8;
 a polarizing system 6;
 a microstructured chip (3; 33; 43; 53; 63) as previously described, placed in the optical path of said incident beam;
 optionally an optical imaging system (9; 69);
 a detector (10; 70).

According to one embodiment, the coupling between the energy of the incident beam and the surface wave of the metal surface of the chip is performed by the chip itself.

According to another embodiment, the coupling means is a prism, a waveguide or a diffraction network.

Thus, according to one particular embodiment, when the coupling is performed by a prism, the chip according to the invention is joined to said prism in such a way that the base of the chip is brought into contact with the upper face of the prism which does not have a metal surface by means of an index matching oil which is a method well-known to those skilled in the art.

According to another embodiment, the chip is joined to a waveguide.

According to yet another particular embodiment, the chip is joined to a diffraction network.

According to the invention, the source 7 may be, for example, a mercury vapor lamp, an incandescence lamp, a laser diode, a laser, a light-emitting diode (LED) or an organic light-emitting diode (OLED).

According to one preferred embodiment, the source 7 is a monochromatic LED. The term "monochromatic" is intended to mean an LED of which the mid-height spectral width does not exceed 40 nm.

According to the invention, various wavelength ranges can be used, such as the visible range or the near infrared (IR) range.

According to one preferred embodiment, a wavelength of between 790 and 825 nm (near IR) is used.

According to the invention, the beam may be collimated. To do this, various techniques well-known to those skilled in the art may be used.

By way of example, use may be made, as optical collimation system 8, of a first convergent lens which makes it possible to focus the light emitted by the source 7 on a hole with a diameter $\Phi$, said hole being in the focal plane of a convergent lens, thereby making it possible to generate the collimated beam.

According to one embodiment, the optical collimation system 8 is integrated into the source 7.

According to the invention, the polarizing system 6 makes it possible to work in transverse magnetic (or TM, or polarization-p) mode.

By way of example, mention may be made of a linear polarizer or a polarizing splitter cube.

According to one preferred embodiment, the polarizing system 6 makes it possible to easily switch from a TM polarization to a TE (transverse electric) polarization, and vice versa. In order to avoid any movement of parts, this can be carried out using a liquid crystal strip, controlled by electric currents and voltages.

According to the invention, the detector (10; 70) may, for example, be a CCD or CMOS camera or may be a photo-detector matrix.

According to one preferred embodiment, the cameras operate on 8, 10, 12 or 16 bits and preferably on 10 or 12 bits.

According to one embodiment, the device also comprises an optical imaging system (9; 69) which makes it possible to produce the image of the microstructured chip (3; 33; 43; 53; 63) on the detector (10; 70).

The optical imaging system (9; 69) must be sufficiently open to accept all the radiations stemming from the microstructured chip. The convex geometry of the n protuberances with which the chip is provided according to the invention especially makes it possible to make the beams converge after reflection of the incident radiation from said protuberances, thus making the optical imaging system (9; 69) much simpler to produce.

Furthermore, the optical imaging system (9; 69) is chosen so that the images of two protuberances or of one protuberance and one cavity of the microstructured chip correspond to two different positions on the detector (10; 70).

Finally, advantageously, the optical system exhibits an enlargement which maximizes the number of useful pixels on the detector (10; 70).

By way of example of an optical imaging system (9; 69), mention may be made of 2 planar-convex lenses mounted afocally.

According to the invention, the face via which an incident radiation enters the chip is referred to as the entry face and the face via which the radiation reflected by the sensitive surface exits is referred to as the exit face.

In FIG. 8, the source 7 emits an incident radiation, which is collimated by means of the collimation system and polarized by means of the polarizer 6 before reaching the entry face 54 of the chip 53 (covered with a metal layer 52)

under a given incidence. The radiation is deflected at its entry into the chip 53 and comes to be reflected on the protuberances 51.

The imaging system 9, located after the exit face 57 of said chip 53, makes it possible to collect the intensity of the reflected radiations and to produce the image of the irradiated protuberances 51 on the detector 10.

The device represented in FIG. 9 comprises a chip 61 (covered with a metal layer 62) of which the side faces are perpendicular to the base and of which the distances between the surfaces separating the protuberances 61 from the base are different from one another.

FIG. 9 represents an embodiment in which the incident radiation emitted by the source (not represented in FIG. 9) which reaches the entry face 64 (corresponding to the side face) perpendicularly, is not deflected when it passes through the chip 63, and irradiates all of the various protuberances 61.

The imaging system 69 and the detector 70 are located after the exit face 67, which, in this embodiment, corresponds to the base of said chip 63, thus making it possible to collect the intensity of the reflected radiations and to produce the image of the protuberances 61.

According to one embodiment, the optical imaging system (9; 69) can be directly integrated into the exit face (57; 67) of the chip (53; 63) in the form of a matrix of microlenses.

According to one preferred embodiment, the collimation system 8 and, optionally, the polarizer 6 are secured to the entry face (54; 64) and/or the optical imaging system (9; 69) and the detector (10; 70) are secured to the exit face (57; 67).

Method of Measurement

Another subject of the invention relates to a method of SPR measurement which comprises the following steps:
  detecting an initial state (i) by irradiating the sensitive surface of at least one of the n protuberances and m cavities via the entry face of the microstructured chip by means of a previously polarized and optionally collimated monochromatic incident beam; and (ii) by simultaneously detecting the intensity of the radiations reflected by the sensitive surface of at least one of said n protuberances and m cavities, exiting via the exit face;
  bringing at least one fluid into contact with the sensitive surface of at least one of said n protuberances and m cavities;
  irradiating the sensitive surface of at least one of said n protuberances and m cavities, containing said fluid, via the entry face of the microstructured chip, by means of a previously polarized and optionally collimated monochromatic incident beam; and simultaneously detecting the intensity of the radiations reflected by the sensitive surface of at least one of said n protuberances and m cavities, exiting via the exit face, so as to continuously monitor, in real time, optical thickness modifications in at least one of said n protuberances and m cavities, with n>0 and m≥0.

Another subject of the invention relates to a method of SPR measurement which comprises the following steps:
  immobilizing ligands on the upper face, covered with a metal layer, of a microstructured chip as previously defined;
  detecting an initial state (i) by irradiating the sensitive surface of at least one of the n protuberances and m cavities via the entry face of the microstructured chip by means of a previously polarized and optionally collimated monochromatic incident beam; and (ii) by simultaneously detecting the intensity of the radiations reflected by the sensitive surface of at least one of said n protuberances and m cavities, exiting via the exit face;
  bringing at least one fluid into contact with the sensitive surface of at least one of said n protuberances and m cavities of said microstructured chip;
  irradiating the sensitive surface of at least one of said n protuberances and m cavities, containing said fluid, via the entry face of the microstructured chip, by means of a previously polarized and optionally collimated monochromatic incident beam; and simultaneously detecting the intensity of the radiations reflected by the sensitive surface of at least one of said n protuberances and m cavities, exiting via the exit face, so as to continuously monitor, in real time, optical thickness modifications in at least one of said n protuberances and m cavities, with n>0 and m≥0.

According to the invention, the immobilization of the ligands on the upper surface can be carried out with various techniques known to those skilled in the art, for instance immobilization by covalent chemical bonding or by electrocopolymerization of pyrrole on the metal surface.

The term "fluid" is intended to mean a gas or a liquid.

According to one preferred embodiment of the invention, the fluid comprises at least one biological species.

These methods of measurement are suitable for measuring, in a nonlimiting manner, conformational variations in molecules immobilized on a surface, biomolecular interactions, optical indices of fluids (gases or liquids), the quality of a surface (parallelism, microscopic roughness, quality of a thin-layer deposit) or of the presence of metal nanobeads in proximity to the surface.

These methods of measurement also make it possible to measure external parameters such as the optical index of the external medium, which makes it possible to work back to the value of the limiting angle of refraction.

According to one embodiment, the incident beam enters perpendicularly via the entry face 64 of the chip 63.

The detection of the intensity of the reflected radiations in the angular range $\Delta\theta$ (or $\Delta\theta'$) by the detector (10; 70) makes it possible to generate all or part of the plasmon curve, the principal zones of interest of which are the following:
  the minimum plasmon sensitivity;
  the angular range in which the sensitivity is highest (i.e. where the derivative of the plasmon is the greatest), also referred to as "flank of the plasmon";
  the zone in the area of the limiting angle of refraction (where things change from a system of refraction to a system of total reflection).

Figure 10:
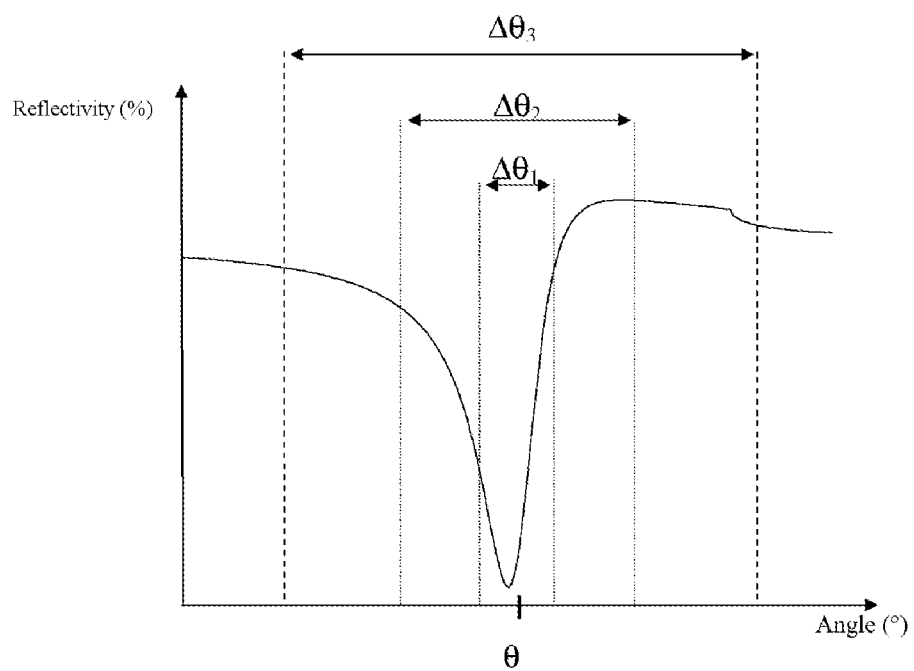
FIG. 10 shows a representative plasmon curve of various angular ranges studied (without tilt).
Figure 11:
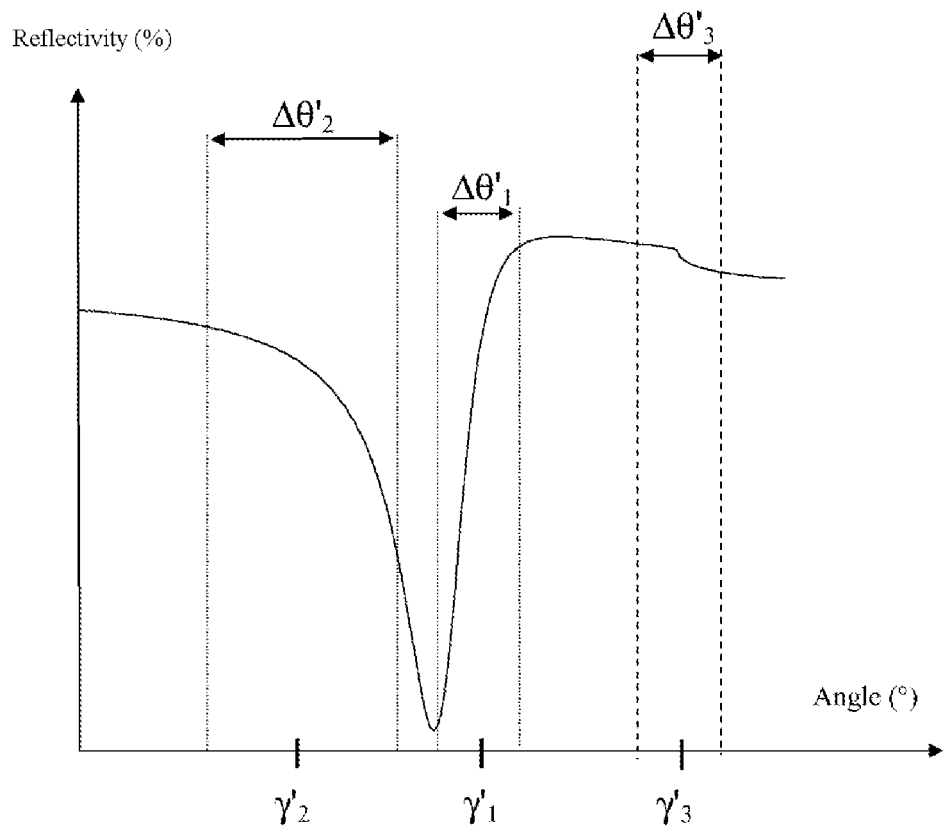
FIG. 11 shows a representative plasmon curve of various angular ranges studied (with tilt).

FIGS. 10 and 11 represent a plasmon curve for 3 zones chosen from n protuberances and m cavities with n+m=3 having different angular study ranges ($1^{st}$ protuberance having an angular range $\Delta\theta_1$ for FIG. 10 and $\Delta\theta'_1$ for FIG. 11, $2^{nd}$ cavity and/or protuberance having an angular range $\Delta\theta_2$ for FIG. 10 and $\Delta\theta'_2$ for FIG. 11 and $3^{rd}$ cavity and/or protuberance having an angular range $\Delta\theta_3$ for FIG. 10 and $\Delta\theta'_3$ for FIG. 11).

FIG. 10 represents the angular ranges of 3 zones chosen from n protuberances and m cavities with n+m=3 when $\beta=0$ (without tilt), while FIG. 11 represents the angular ranges of 3 chosen from n protuberances and m cavities with n+m=3 when $\beta\neq 0$ (with tilt).

In FIG. 10, i.e. when $\beta=0$ (without tilt), the 3 angular ranges studied are centered on the angle $\theta$. The width of each of the zones is defined by the angle at the apex $2\alpha$ and the radius of curvature R of each of the protuberances or protuberances and cavities. The choice of the angle θ is therefore essential for observing all the zones of interest as well as possible. It is thus possible, according to the radius of curvature of the zones studied, to explore a more or less large angular range of the plasmon curve. In the case where the zones do not exhibit any tilt θ (this is the case for FIG. 10), this angular range will always be centered on the same value θ.

In FIG. 11, i.e. when θ≠0 (with tilt), the three angular ranges $\Delta\theta'_1$, $\Delta\theta'_2$ and $\Delta\theta'_3$ are centered respectively on the angles $\gamma'_1$, $\gamma'_2$ and $\gamma'_3$, said angles $\gamma'_1$, $\gamma'_2$ and $\gamma'_3$ each being defined by different angles β. In this situation (with tilt), the angular ranges are not centered on the same value. It is thus possible to explore a variable angular range of the plasmon curve while having an incident beam at a single angle, thus making it possible not to need the mobile parts normally used for performing an angular rotation of the incident beam.

According to another embodiment, the method of measurement also comprises a step in which an image of the n protuberances and the m cavities of the chip is produced.

Figure 12:
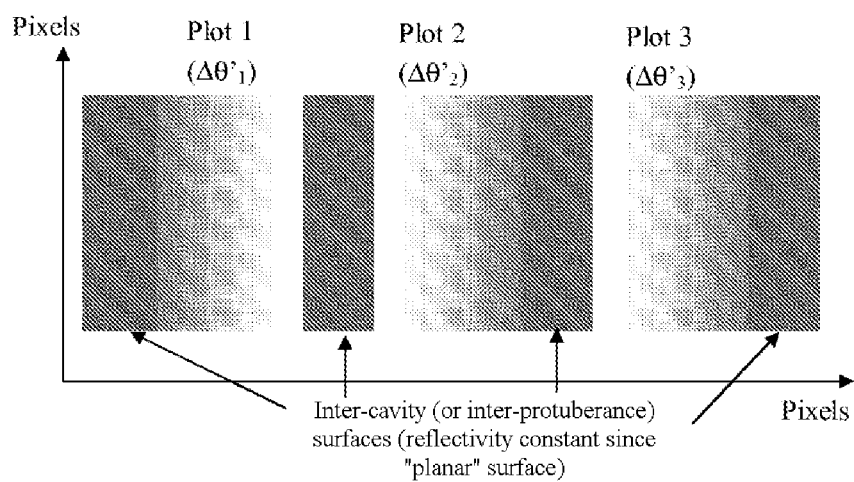
FIG. 12 represents an example of an image on a camera of 3 protuberances of a microstructured chip according to the invention.

FIG. 12 represents the image of the 3 zones chosen from n protuberances and m cavities with n+m=3 (plasmon curve of FIG. 11) on a matrix detector in which the dark band between the luminous bands (gray shading) represents the inter-cavity and/or inter-protuberance surfaces which have a constant reflectivity since they are planar surfaces.

According to the invention, it is thus possible, knowing the incident angle θ which is constant and fixed by the architecture of the optical system (since no mechanical part is moving), to choose the angular range Δθ that will optionally be imaged on the detector (by choosing the radius of curvature R and the angle α, or the radius of curvature R and the diameter d, since α and d are deduced from one another by virtue of the radius of curvature R) and the mean angle $\gamma'_{mean}$ (with the choice of the tilt β) of the microstructure according to the various species to be analyzed with $\gamma'_{mean}=\theta+2\beta$. This choice can be made for each of the n protuberances and the m cavities, thereby making it possible to adapt to several types of species immobilized on the same chip.

Likewise, the choice can be made according to the type of species that will interact with the species previously immobilized on the chip: it is thus possible to "adapt" each of the protuberances or protuberances and cavities to the species sought.

Thus, another subject of the invention relates to the use of the device according to the invention for measuring biomolecular interactions.

The invention is illustrated by means of the examples which are given solely by way of illustration and are not limiting.

EXAMPLE 1

Figure 13:
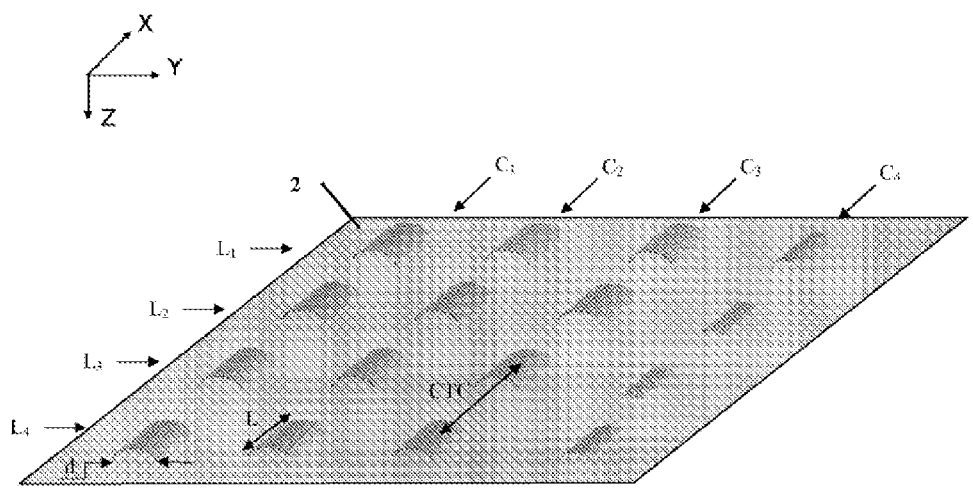
FIG. 13 represents a chip according to the invention comprising 16 cavities, at least one of which is different from the others.

Protein Chip—Monitoring and Correction of the Index of the External Medium in Real Time in Interaction Kinetics A microstructured chip made of polycarbonate (PC) comprising 16 protuberances is represented in FIG. 13.

A layer of gold which has a thickness of 48 nm was deposited by sputtering on the upper face of said chip in order to obtain a plasmon effect.

In TM polarization, the minimum reflectivity is obtained around the angle θ=28°.

The 16 protuberances are distributed according to a regular matrix of 4×4 semi-cylindrical surfaces having a diameter d=500 µm and a length L=500 µm, each one spaced out by a center-to-center (CTC) distance of 1 mm.

Four different species were covalently immobilized by virtue of an electropolymerization of a film of polypyrrole functionalized with the ligands of interest.

Thus, the following species present in the protuberances are:
on line $L_1$: monoclonal anti-mouse antibodies,
on line $L_2$: monoclonal antibodies directed against human chorionic gonadotropin hormone (hCG, involved as a biomarker in several cancer pathologies),
on line $L_3$: monoclonal antibodies directed against the bacterium *Listeria monocytogenes*,
on line $L_4$: BSA (bovin serum albumin).

The chip is irradiated with a polarized, collimated and monochromatic incident radiation and the intensity of the radiations reflected by the protuberances is detected by a CMOS detector.

The radius of curvature of the semi-cylindrical surfaces of the protuberances of columns $C_1$, $C_2$ and $C_3$ is 9.5 mm (equivalent to an angular study zone $\Delta\theta_a$ on the plasmon curve of approximately 3°) and the protuberances of column $C_4$ have a radius of curvature of 1.9 mm (equivalent to an angular study zone $\Delta\theta_b$ of approximately 15°). The angular ranges $\Delta\theta_a$ and $\Delta\theta_b$ correspond respectively to the angular ranges $\Delta\theta_1$ and $\Delta\theta_3$ in FIG. 10.

A liquid with an unknown optical index, containing hCG proteins, is brought into contact with the chip in the protuberances. A characteristic variation in the signal is observed as a function of time on the protuberances of line $L_2$, but not on the others since a specific interaction takes place on the anti-hCG monoclonal antibodies and not on the other immobilized proteins.

Furthermore, since the protuberance located at ($L_2$, $C_4$) has a radius of curvature such that the entire plasmon curve can be visualized on the detector, the angular value of the limiting angle of refraction can be easily determined and it is thus possible to deduce the unknown index of the liquid medium.

Thus, knowing this index, it is possible to accurately determine the variation in the signal on the protuberances located at ($L_2$,$C_1$), ($L_2$,$C_2$) and ($L_2$,$C_3$), by decorrelating the variation in signal associated with the external medium from the variation in signal associated with the attachment of hCG proteins to the anti-hCG monoclonal antibodies.

EXAMPLE 2

Chip for Studying Shiga Toxin-producing *Escherichia coli* Bacteria

In this example, the presence of shiga toxin-producing *Escherichia coli* (STEC) bacteria in a sample stemming from the food-processing industry was studied.

Examples of bacteria of this category are the O157:H7, O26:H11 or else O103:H2 strains. The bacteria of this type and the shiga toxins that they produce are responsible for severe intestinal problems, which may be life-threatening. The size and the molecular weight of these shiga toxins (a few nanometers in diameter and a molecular weight of approximately 68 kDa) is very different from that of an *Escherichia coli* bacterium (approximately 10 million times heavier). Consequently, the plasmon signals for the attachment of these two types of families are very different. With conventional SPR devices, it is not therefore possible to study both these bacteria and these toxins in the same experiment and in real time. This is because, in the case of the attachment of bacteria, the curve will shift angularly by close to 0.1°, whereas it will only move by less than 0.01° in the case of toxins (which is not easily detectable by conventional SPR methods).

This example demonstrates that, by using a microstructured chip according to the invention which has a particular architecture, it is possible to study these two biological species of different sizes during a single experiment.

A chip made of polycarbonate, comprising two semi-cylindrical protuberances, 600 μm in diameter and 800 μm long, is produced.

The upper face of said chip is covered with a layer of chromium having a thickness of 2 nm and with a layer of gold having a thickness of 48 nm, both deposited by sputtering in order to obtain a plasmon effect.

The first protuberance exhibits a zero tilt ($\beta=0$) and the second protuberance exhibits a tilt of value $\beta=0.5°$.

The chip is irradiated with a polarized, collimated and monochromatic incident radiation and the intensity of the radiations reflected by the sensitive surface of the protuberances is detected by a CCD detector.

The mean angle of incidence of the optical system is mechanically fixed by the architecture of the system and is equal to 26.5°.

Figure 14:
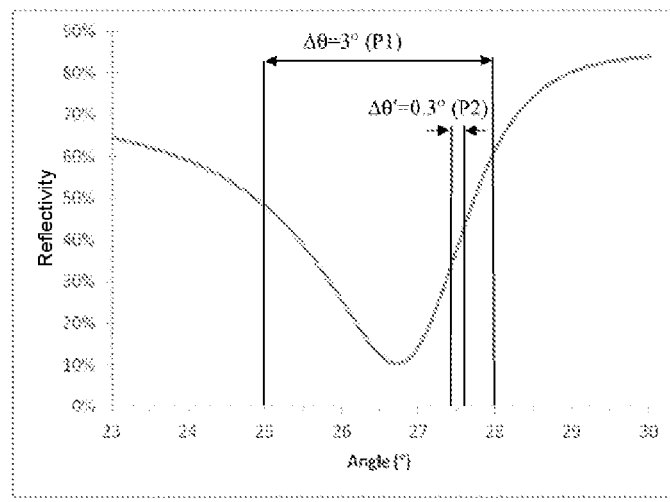
FIG. 14 represents the percentage reflectivity as a function of the angle of incidence θ.

The radius of curvature of the two protuberances is also different: 11.5 mm for the first protuberance (corresponding to an angular study range $\Delta\theta$ of 3°) and 100 mm for the second (which corresponds to an angular analysis range $\Delta\theta'$ of 0.3°) (FIGS. 14).

Monoclonal antibodies directed against the O157:H7 bacterium are covalently and uniformly immobilized on the first protuberance, and monoclonal antibodies specifically directed against the shiga toxins that the bacterium secretes are immobilized on the second protuberance.

The two plasmon curves generated from these two protuberances exhibit the same plasmon resonance angle (approximately 26.7°), before reaction.

When a mixture containing a large amount of O157:H7 bacteria is brought into contact with the sensitive surface of the chip (in other words on the protuberances), some of them interact specifically with the antibodies of the first protuberance. Since bacteria are molecules that are detected well by SPR (owing to their heavy weight), the plasmon curve shifts sufficiently for this shift to be picked up very well by the detector imaging the first protuberance. Moreover, this bacterium also secretes shiga toxins during the same experiment.

Figure 15:
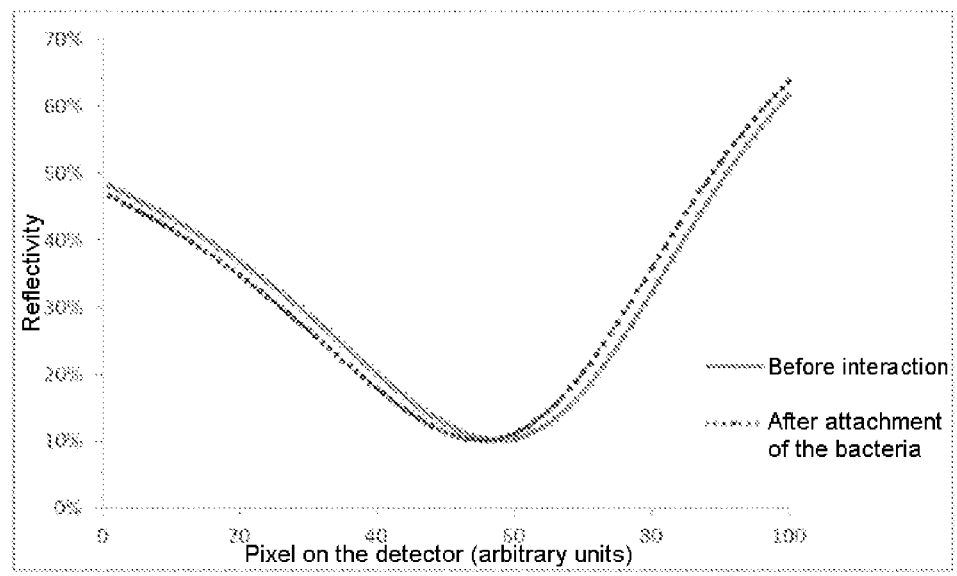
FIG. 15 represents the plasmon curves before and after attachment of the *Escherichia coli* bacterium on the protuberances functionalized with ligands specific for the bacterium.
Figure 16:
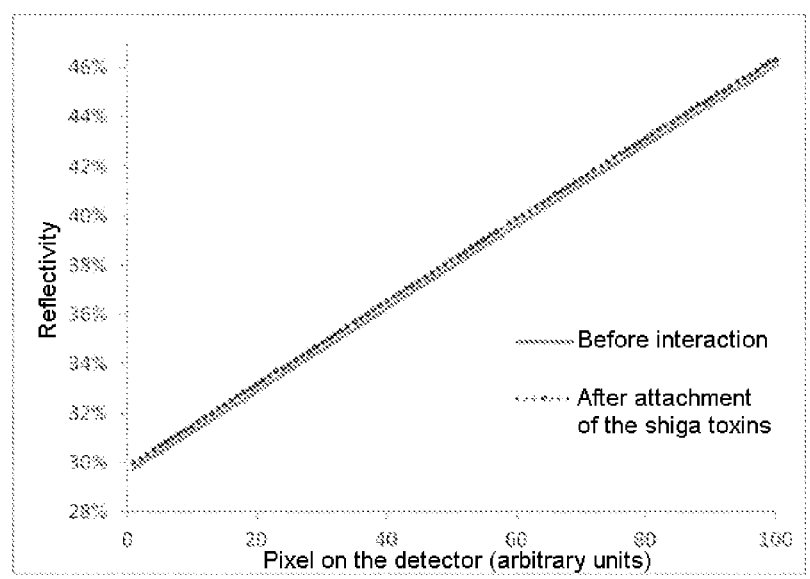
FIG. 16 represents the plasmon curves before and after attachment of the shiga toxins on the protuberances functionalized with ligands specific for the shiga toxins.

The second protuberance exhibits a slight tilt ($\beta=0.5°$) and a much smaller angular width studied ($\Delta\theta'=0.3°$). Thus, the measurement sensitivity of the second protuberance is greater and it is possible to detect shiga toxins which bind to the antibodies of the second protuberance. FIGS. 15 and 16 represent the signals obtained on the detector for the two protuberances before and after interaction of the antibodies immobilized on each of the protuberances with, respectively, the bacteria and the toxins.

Thus, this example demonstrates that the chip according to the invention makes it possible to adjust the measurement dynamics and sensitivity to the species to be measured during a single experiment.

The invention claimed is:

1. A microstructured chip (3; 33; 43; 53; 63) for surface plasmon resonance (SPR) analysis, comprising:
   a solid consisting of a base (5; 77), an upper face (4; 44), and at least one side face (55; 66);
   a metal layer (2; 22; 42; 52; 62) that covers at least one part of the upper face; and
   zones of micrometric size provided on the upper face, the zones having at least two of i) a length dimension, ii) a width dimension, and iii) a height dimension ranging from 1 μm to 1000 μm, the zones being intended to receive species to be analyzed, the zones comprising n protuberances and m cavities, wherein n+m≥2, and said zones are separated from one another by planar surfaces, with n ranging from 1 to j and m ranging from 0 to i, j and i being integers,
   wherein each of the n protuberances and each of the m cavities (1; 11; 41; 51; 61) comprise a curved surface with a radius of curvature ("R"), between 0.1 and 600 mm.

2. The microstructured chip (3; 33; 43; 53; 63) according to claim 1, wherein the radius of curvature ("R") of each of the n protuberances and the m cavities (1; 11; 41; 51; 61) is identical.

3. The microstructured chip (3; 33; 43; 53; 63) according to claim 1, wherein the radius of curvature ("R") of at least one of the n protuberances and the m cavities (1; 11; 41; 51; 61) is different from the radius of curvature ("R") of all other ones of the n protuberances and the m cavities.

* * * * *